US006418788B2

(12) United States Patent
Articolo

(10) Patent No.: US 6,418,788 B2
(45) Date of Patent: Jul. 16, 2002

(54) DIGITAL ELECTRONIC LIQUID DENSITY/LIQUID LEVEL METER

(76) Inventor: George A. Articolo, 67 Farnwood Rd., Mt. Laurel, NJ (US) 08054

( * ) Notice: Subject to any disclaimer, the term of this patent is extended or adjusted under 35 U.S.C. 154(b) by 0 days.

(21) Appl. No.: 09/739,832

(22) Filed: Dec. 20, 2000

Related U.S. Application Data

(60) Provisional application No. 60/185,190, filed on Feb. 25, 2000.

(51) Int. Cl.[7] .............................................. G01F 23/30
(52) U.S. Cl. ............................ 73/314; 73/319; 340/623
(58) Field of Search ............................... 73/290 R, 861, 73/453, 309, 291, 304 R, 305, 308, 304 C, 314

(56) References Cited

U.S. PATENT DOCUMENTS

| | | | | |
|---|---|---|---|---|
| 3,089,502 A | * | 5/1963 | Davidson et al. ............. 137/90 |
| 3,954,010 A | | 5/1976 | Hilblom ........................ 73/291 |
| 3,964,317 A | | 6/1976 | Blanchard ..................... 73/453 |
| 4,015,477 A | | 4/1977 | Sitkewich ..................... 73/398 |
| 4,400,978 A | | 8/1983 | Guay et al. ................... 73/453 |
| 4,571,998 A | * | 2/1986 | Stegner ........................ 73/321 |
| 4,589,282 A | * | 5/1986 | Dumery ........................ 73/313 |
| 4,742,811 A | * | 5/1988 | Okada et al. ................. 123/643 |
| 4,791,311 A | * | 12/1988 | Vig ........................... 307/10 R |
| 4,850,223 A | * | 7/1989 | Carlin et al. .................. 73/49.2 |
| 4,912,646 A | * | 3/1990 | Cerruti ........................ 364/509 |
| 4,920,797 A | * | 5/1990 | Swartz et al. ................. 73/309 |
| 4,981,042 A | | 1/1991 | Reeves ........................ 73/454 |
| 5,253,522 A | * | 10/1993 | Nyce et al. ................... 73/453 |
| 5,447,063 A | | 9/1995 | Glassey ........................ 73/437 |
| 5,471,873 A | * | 12/1995 | Nyce et al. ................... 73/453 |
| 5,744,701 A | * | 4/1998 | Peterson et al. ............. 73/49.2 |
| 5,744,716 A | | 4/1998 | Mimken et al. ............... 73/453 |
| 5,815,091 A | * | 9/1998 | Dames et al. .......... 340/870.34 |
| 5,847,276 A | | 12/1998 | Mimken et al. ............... 73/453 |

* cited by examiner

Primary Examiner—Hezron Williams
Assistant Examiner—Rodney Frank
(74) Attorney, Agent, or Firm—Foley & Lardner

(57) ABSTRACT

A liquid density/liquid level meter includes a spring-float system that is coupled with a multiple Hall-sensor configured linear displacement transducer. The spring-float system includes springs that constrain the movement of floats on each end; the spring-float system parameters are mathematically evaluated so as to meet precise performance criteria. The linear displacement transducer includes a magnet and the Hall sensors. The linear displacement transducer and the spring-float system are coupled together within a submerible head unit. When the head unit is immersed in the liquid, the spring-float system moves the magnet, which interacts with the Hall sensors in a lateral slide-by approach that produces an analog voltage that is continuous and linear with respect to the displacement of the magnet. The output from the head unit is communicatively connected to a remote electronic module that contains a signal conditioner with a digital readout. There are two possible operating applications of this device that depend upon the two possible configurations of the floats in the system. In the liquid density application-configuration, at least two floats are used and the device is initialized to give a direct measure of the density (specific gravity) of the liquid. In the liquid level application-configuration, a single float is used and the device is initialized so as to give a continuous direct measure of the level of the liquid within a container.

18 Claims, 7 Drawing Sheets

Liquid level application-configuration submersible head unit.

Liquid density application-configuration submersible head unit.

Liquid level application-configuration submersible head unit.

DIGITAL ELECTRONIC LIQUID DENSITY/ LIQUID LEVEL METER

RELATED APPLICATIONS

This application is related to provisional application No. 60/185,190, filed Feb. 25, 2000, to which this application is entitled to claim priority to.

BACKGROUND OF THE INVENTION

1. Field of the Invention

This invention is directed to a Hall sensor configured linear displacement transducer which contains magnet that is float activated by way of a spring-float system with precise magnitudes of liquid buoyancy, spring constants, and float density. Together, the linear displacement transducer and the spring-float system combine to form a submersible head unit of this device. The analog output voltage of each of the Hall sensors within the head unit are communicatively connected (either by wired or by wireless connection) to a remote electronic signal conditioner. Depending upon the operational configuration of the floats in the system and the original initialization of the device, the electronic conditioned signal provides two possible measures. When the head unit is configured as a liquid density meter and is completely immersed in a liquid, the combination of the submersible head unit and the electronic signal conditioner constitutes the liquid density meter that provides for measuring and monitoring the density (specific gravity) of the liquid. When the head unit is configured as liquid level meter and is immersed in a container which hold the liquid, the combination of the submersible head unit and the electronic signal conditioner constitutes the liquid level meter that provides for measuring and monitoring the level (height) of the liquid in the container.

2. Description of the Related Art

There are many different types of devices that use different technologies to measure either the density of a liquid or the level of a liquid in a container. In this invention, the basic operating principle of either application can be categorized as being a float-activated device that is responsive to the buoyancy force of the float in the liquid. From physics, the buoyancy force produced by a float in a homoglneous liquid is equal to the weight of the liquid that is displaced by the float. Since buoyancy force is linear with respect to the density of the liquid within which the float is submerged, the measure of the buoyancy force yields a measure of the density of the liquid. Further, since buoyancy force is linear with respect to the volume of liquid displaced by the float within the liquid, then the measure of buoyancy force of a float within a liquid within a container yields a measure of the level (height) of the liquid within the container.

The measure of buoyancy force produced by a float in a liquid is generally dependent upon the measure of the displacement of the float within the liquid by way of a displacement transducer. The liquid density/liquid level meter in this invention uses a distinctive linear displacement transducer that is based on the operating principles of Hall sensors. This distinctive linear displacement transducer is coupled with a spring float system whose parameters meet precise performance criteria.

Discussed below are many conventional liquid density or liquid level measuring devices that are based on the principle of a float-activated system. In a general sense, they differ from each other in regards to the different transducer means that each one utilizes for detecting the relative position of the float in the liquid.

In U.S. Pat. No. 3,089,502, a conventional hydrometer bulb acts as a float that activates the position of a magnetic core of a differential transformer whose output voltage monitors the position of the bulb so as to measure the liquid density.

In U.S. Pat. No. 3,954,010, a float activates the on/off position of the sight line of a beam of light into a light sensor and this is the means for detecting the position of the float in the liquid.

Both U.S. Pat. No. 3,964,317 and U.S. Pat. No. 4,400,978 utilize a similar principle whereby a float activates the position of an electrical sensing coil that is in the vicinity of a stationary magnet. A force-balance restoring current is established in the coil to restore the coil to a neutral position and the magnitude of this current is a measure of the buoyancy force and density of the liquid.

In U.S. Pat. No. 4,015,477, a float activates the position and radius of curvature of a magnetostrictive sensitive wire that is electrically sensed to measure the displacement of the float and, thus, the buoyancy force of the liquid.

In U.S. Pat. No. 4,981,042, a float activates the position of a lever that is connected to the float by way of a pivot assembly. The position of the lever is sensed electronically to measure the displacement of the float to determine the buoyancy force and, thus, the density of the liquid.

In U.S. Pat. Nos. 5,253,522 and 5,471,873, a float activates the position of a toroidal magnet that surrounds a sonic waveguide. A reference magnet also surrounds the waveguide and is positioned at a distance away from the float magnet. An electrical impulse wave is sent along the waveguide and both magnets provide a reflected torsional (magnetostrictive) pulse. The time difference between the reflected signals from the two magnets is indicative of the relative position of the float in the liquid and, thus, the buoyancy force and density of the liquid.

In U.S. Pat. No. 5,447,063, a float activates the tilt of one end of a balance beam. A sensor employs a differential transformer to detect the magnitude of the tilt, thus providing a measure of the buoyancy force and density of the liquid.

In U.S. Pat. Nos. 5,744,716 and 5,847,276, a float activates a pair of force transducers that give a direct measure of the buoyancy force and, thus, the density of the liquid.

U.S. Pat. No. 4,920,797 describes a liquid level sensor with a spring-float assembly and a displacement transducer. In U.S. Pat. No. 4,920,797, two springs hold a single float, which activates the position of a magnet in the vicinity of a Hall sensor.

In addition to the principle of float-activated systems, there are many other different technical approaches to measuring either liquid density or liquid level. Briefly, they are refractive index, vibrating tube, capacitive, vibrating plate, vibrating pipe, radiation, differential pressure, Coriolis meter, inductance coil, and bubble probe.

SUMMARY OF THE INVENTION

This invention utilizes a linear displacement transducer whose operating principle is based on the voltage-generating characteristic of Hall sensors. Hall sensors are devices that produce a voltage that is proportional to the magnitude of the transverse magnetic field that intercepts the sensitive plane of the sensor. Edwin H. Hall first discovered the Hall principle (reference: R. P.Winch, Electricity and Magnetism, 1963, Prentice Hall) in 1879.

The Hall sensor linear displacement transducer acts as the proximity-sensing element in the operation of this invention.

Hall sensors (two or more) are configured on a non-magnetic sensor fixture assembly such that the sensors are equal-angularly spaced about the circular periphery of the cylindrical sensor fixture. Within the sensor fixture is a concentric borehole that allows for a nonmagnetic actuator rod to move axially between the Hall sensors. An axially aligned permanent magnet is embedded within the actuator rod. The Hall sensors provide an output voltage that is proportional to the magnitude of the radial (transverse) magnetic field that intercepts the sensitive plane of the sensor. As the magnet moves axially in a lateral slide-by approach with respect to the sensors, each of the sensors generates an output voltage that is continuous and linear with respect to the displacement.

A cylindrical (or a rectangular) permanent bar magnet is used in this invention to provide the magnetic field for the Hall sensors. The magnetic field associated with a permanent magnet depends upon the geometry and the magnetization of the magnet. In addition, the magnitude and the direction of the magnetic field depend upon the point of observation with respect to the magnet. From a head-on observation of the field on the longitudinal axis at a distance from one of the poles of the magnet, the field has a direction that is parallel to the longitudinal axis and a magnitude that drops off non-linearly as the reciprocal of the square of the distance. On the other hand, at the lateral sides of the magnet, within the confines of the ends (within 80% of the magnet length), the field has a radial (transverse) component that is linear with respect to the longitudinal axial distance as measured from the center of the magnet. It is this field characteristic that is utilized in the preferred embodiment as the actuator rod moves the magnet in a lateral slide-by approach between the Hall sensors within the sensor fixture assembly.

As the magnet moves axially within the confines of the sensor fixture, the lateral alignment between the magnet and each Hall sensor varies because of possible misalignments of the machine-produced mechanical parts in the assembly—it is extremely difficult if not impossible to produce machined parts that have perfect alignment and dimensions. For the special case of two sensors positioned diametrically opposite each other, as the actuator rod moves the magnet through the sensor fixture, there are instances when the magnet pushes towards one Hall sensor while at the same time it pulls away from the other. This effect gives rise to the two diametrically opposite Hall sensors producing a push-pull variation in output voltages—the push-pull effect. To compensate for any of this built in misalignment, the output voltages of the Hall sensors used in this invention are mixed in a dedicated signal conditioner that averages the voltages, consequently canceling out this push-pull effect. Two or more Hall sensors can be configured within and about the sensor fixture to compensate for this push-pull variation by adhering to the constraint that the sensors be equal-angularly spaced about the circular periphery of the fixture; i.e. for two sensors, 180 degree spacing, for three sensors, 120 degree spacing, etc.

When the submersible head unit is immersed in the liquid, the spring-float system provides the mechanism that moves the magnet into the proximity detection region of the linear displacement transducer described above. There are two possible configurations of the spring-float system which gives rise to two possible operating applications of this device.

In the liquid density application-configuration, where the device is used to measure the density of a liquid, two cylindrical floats are coupled together with the actuator rod in-between the two. In the liquid level application-configuration, where the device is used to measure the level of a liquid, only a single cylindrical float is used to hold the actuator rod on one end. In both configurations, springs are used to constrain the movement of the float-rod system within the cylindrical tube that contains the liquid. Guides force the actuator rod, to ride concentrically within the interior of the borehole of the sensor fixture. When the spring-float system is immersed vertically in a liquid, it forces the rod to rise in accordance to the combination values of the buoyancy force of the liquid, the spring constants, and the density of the floats (float). The rise of the floats (float) and the attached actuator rod produces a displacement of the embedded magnet into the proximity detection region of the linear displacement transducer.

In the liquid density application-configuration, where the device is used to measure the density of a liquid, since the displacement of the spring supported floats is linear with respect to the buoyancy force, and the buoyancy force of the liquid is linear with respect to the density of the liquid, then the displacement of the magnet is linear with respect to the density of the liquid. The transducer converts this displacement, by way of a dedicated signal conditioner, into an equivalent linear voltage that is a direct measure of the density (specific gravity) of the liquid.

The liquid density measuring configuration of this invention is based upon the floatation principle of a spring-float system, with an actuator rod and an embedded magnet, that has a preferred mathematical combination of values of buoyancy force, float density, and spring constant. The spring-float system parameters are mathematically evaluated so as to meet the following precise performance criteria: the combined buoyancy force produced by the floats and actuator rod, when totally immersed in pure water (specific gravity equal to 1), equals the combined sum of the gravitational weights of the floats and the actuator rod and the magnet, when measured in air, plus the total spring force exerted on the floats when this combination hangs on the two springs in air.

In the liquid level application-configuration, where the device is used to measure the level of a liquid, since the displacement of the spring supported float is linear with respect to the buoyancy force of the liquid, and the buoyancy force of the liquid is linear with respect to the level of penetration of the cylindrical float within the liquid, then the displacement of the magnet is linear with respect to the level of the liquid in the container. The transducer converts this displacement, by way of a dedicated signal conditioner, into an equivalent linear voltage that is a direct measure of the continuous level (height) of the liquid within the container.

The liquid level measuring configuration of this invention is based upon the floatation principle of a spring-float system, with an actuator rod and an embedded magnet, that has a preferred mathematical combination of values of buoyancy force, float density, and spring constant. The spring-float system parameters are mathematically evaluated so as to meet the following precise performance criteria: the combined buoyancy force produced by the float and actuator rod, when totally immersed in the particular liquid, equals the combined sum of the gravitational weights of the float and the actuator rod and the magnet, when measured in air, plus the total spring force exerted on the float when this combination hangs on the two springs in air.

The coupling together of the spring-float system and the linear displacement transducer described above constitute the submersible head unit of this invention. The mechanical and geometrical configuration of the spring-float system and the linear displacement transducer is provided in the detailed description of the preferred embodiments below. The analog output voltages from the Hall sensors within the linear displacement transducer are input, by way of electrical wires (or by wireless transmission in an alternative configuration), into a remote electronic signal conditioner. Depending upon the configuration of the head unit as a liquid density meter or a liquid level meter, the conditioned electronic signal gives a particular application measurement. As a liquid density meter, the conditioned signal provides a direct measure of the density (specific gravity) of the liquid. As a liquid level meter, the conditioned signal provides a direct measure of the continuous level (height) of a liquid in a container. A thermocouple (temperature sensor) can be attached to the submersible head unit of this invention, thus allowing for monitoring the temperature of the liquid.

BRIEF DESCRIPTION OF THE DRAWINGS

The invention will become more fully apparent from the following detailed description when read in conjunction with the accompanying drawings with like reference numerals indicating corresponding parts throughout, and wherein.

DETAILED DESCRIPTION OF THE PREFERRED EMBODIMENTS

Preferred embodiments of the present invention will be described in detail hereinbelow, with reference to the drawings. Of the references discussed in the "Background of the Invention" section, U.S. Pat. No. 4,920,797 appears to be the most relevant. At least some of the differences between the present invention and the system described in U.S. Pat. No. 4,920,797 are described below.

In U.S. Pat. No. 4,920,797, wafer thin spiral (leaf) springs are used versus conventional helical or conical springs used in this invention. In U.S. Pat. No. 4,920,797, the approach of the magnet to the Hall sensor is a head-on approach whereby the sensitive plane of the Hall sensor is at right angles to the longitudinal axis of the magnet. Since the magnetic field in a head-on approach falls off inversely as the square of the axial distance from the pole face, the output voltage of the Hall sensor in this head-on approach is, likewise, proportional to the inverse square of the distance between the sensor and the magnet. This inverse square relation is not desirable since it does not provide a linear relation between the displacement and the output voltage. The present invention is novel in that the Hall sensors are mounted laterally off to the sides of the magnet in the preferred lateral slide-by approach whereby the sensitive plane of the sensors is parallel to the longitudinal axis of the magnet, not at right angles. In this lateral slide-by approach, the radial (transverse) component of the magnetic field is linear with respect to the axial displacement measured from the center of the magnet; thus, the output signal of each sensor is linear with respect to the displacement. The characteristic of linearity is the preferred hallmark of the particular displacement transducer used in this invention.

Figure 1:
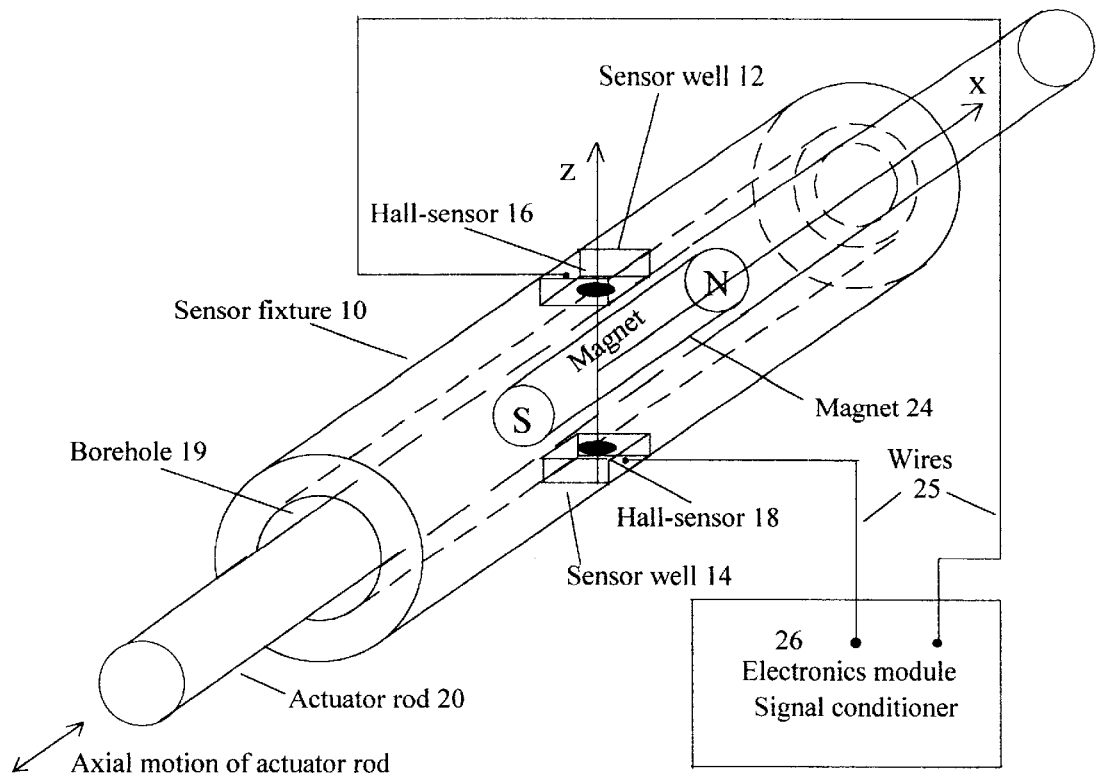
FIG. 1 is a diagram of the sensor fixture that holds the Hall sensors (by way of example but not by way of limitation, only two sensors are used) and the actuator rod that holds the embedded magnet.

In FIG. 1, a non-magnetic cylindrical (other shapes are possible, such as rectangular) sensor fixture 10 contains two or more (for purposes of this simplified description here, two are used) sensor wells 12 and 14 that hold two Hall-effect sensors 16 and 18. Hall effect sensors are small electronic devices that produce output voltages that are proportional to the magnitude of the transverse magnetic field that intercepts the sensitive plane of the sensors. For the case of two sensors, the two sensors 16 and 18 are located diametrically across from one another (180 degrees) on the sensor fixture. Within the interior of the cylindrical sensor fixture is a concentric cylindrical borehole 19 within which a non-magnetic actuator rod 20 is allowed to slide axially along the positive and negative direction of the longitudinal x-axis. As the actuator rod 20 is allowed to move axially, it is also forced to remain concentric with respect to the cylindrical borehole 19 within the cylindrical sensor fixture 10. Embedded within the actuator rod 20 is a cylindrical permanent bar magnet 24. As the actuator rod 20 moves, the magnet 24 slides, by and between, the two Hall sensors 16 and 18. Since the relative axial position of the bar magnet 24 changes with respect to the fixed positions of the Hall sensors 16 and 18, the varying transverse magnetic field, which intercepts the sensitive plane of the Hall sensors, produces a corresponding varying output voltage from each sensor. Because the radial (transverse) component of the intercepted magnetic field varies linearly with respect to the relative longitudinal positions of the magnet and the sensors (within 80% of the length of the magnet), the corresponding output voltages of the two sensors also vary linearly. The two Hall sensors are connected by way of electrical wires 25 into an electronics module 26 that contains a signal conditioner and the power source for operation of the Hall sensors. The signal conditioner averages the two, or more, sensor voltages. The preferred act of averaging the voltages provides compensation to offset the deleterious effects due to any possible misalignment in the lateral displacements between the sensors and the magnet 24 as the magnet slides through the interior of the sensor fixture 10. If there is any misalignment then, since the sensors are diametrically opposite each other for the case of two sensors, as the magnet pushes closer to one sensor, it correspondingly pulls away from the other sensor -the push-pull effect. Since the average of the lateral displacements is a constant, then the averaging circuit provides an output voltage that is independent of any misalignment and the voltage varies linearly with respect to only the axial x-position of the magnet as it moves. If more than two sensors are used, then this push-pull effect is correspondingly handled by a sensor configuration whereby the sensors are equal-angularly spaced about the circular periphery of the sensor fixture.

Figure 2:
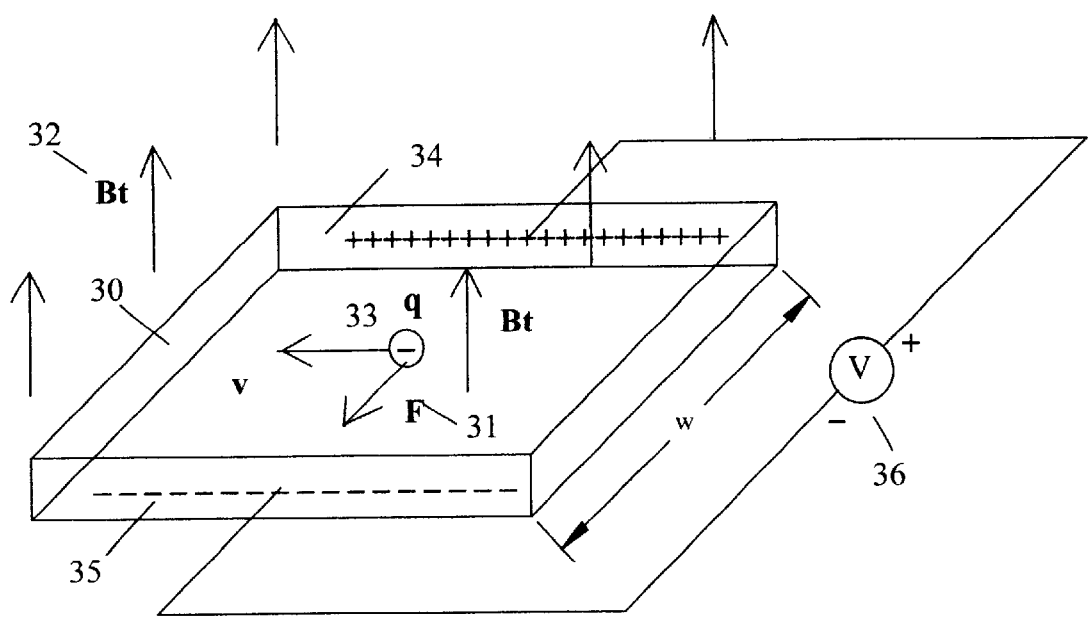
FIG. 2 is a diagram that shows the orientation of the sensitive plane of the Hall sensors with respect to the radial (transverse) magnetic field of the bar magnet.

The Hall-sensors operate on the principle of the Hall effect, which is the production of an electric field and a corresponding voltage difference across the sides of a current carrying conductor whose sensitive plane is intercepted by a non-zero transverse magnetic field. Hall sensors are very small devices (typically on the order of $\frac{1}{16}$ inch square). In FIG. 2, a blown up view is shown of a typical Hall sensor. The Hall sensor includes a flat conductor 30 that is immersed in an upward directed transverse magnetic field Bt 32; the sensitive plane of the conductor is at right angles to the direction of the field. An electric current flows through the conductor and this is symbolized by the negative charge q 33 moving with velocity v from right to left. Due to the presence of the transverse magnetic field, the charges in the current experience a force F 31, given as the vector cross product F=qv×Bt. This force is cause for the electrons to migrate to the lower portion of the conductor, thus leaving a net imbalance of negative charge (−) on the bottom face 35 and a corresponding equal positive charge (+) on the top face 34. This charge separation gives rise to an electric field E, the magnitude of which is given as the vector cross product E=−v×Bt. If the width of the conductor is w, then the resulting voltage potential difference between the faces 34 and 35 of the conductor, as measured by the voltmeter V 36, is given as the scalar product magnitude V=vwBt where Bt is the magnitude of the vector Bt. This potential difference can be measured and, clearly, since Bt=V/(vw), then the voltage potential difference V 36 is a measure of the magnitude of the transverse magnetic field Bt.

Figure 3:
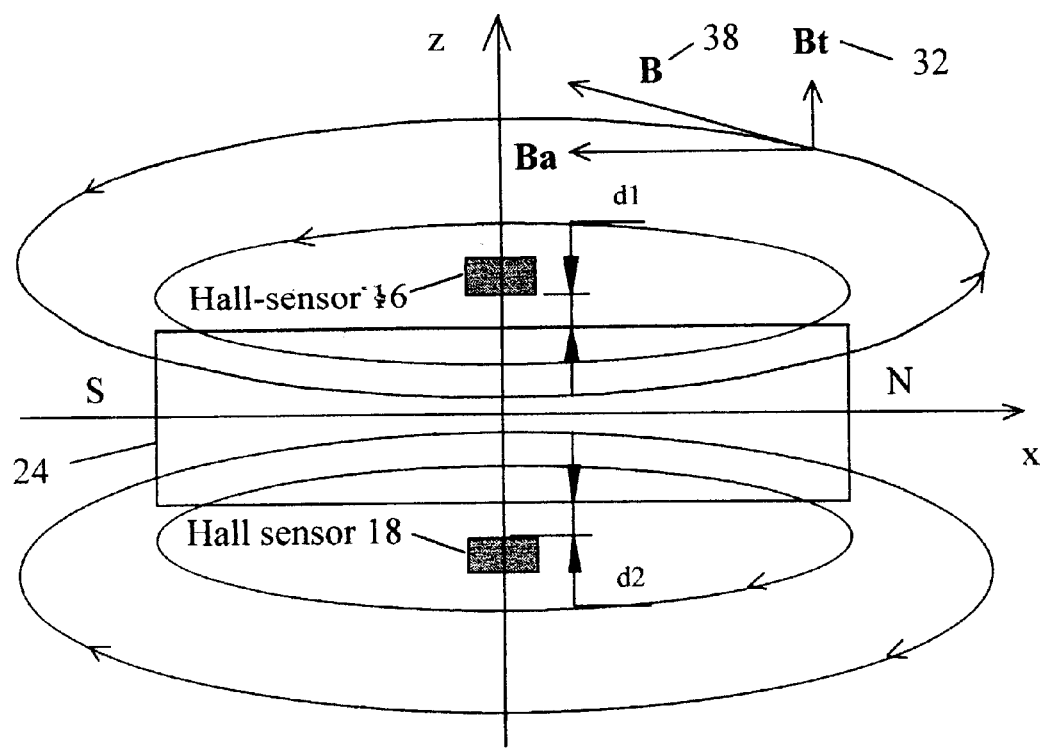
FIG. 3 is a diagram that shows the preferred embodiment of the Hall sensors and the vector components (radial and axial) of the magnetic field of the bar magnet when configured in a lateral slide-by approach.
Figure 4:
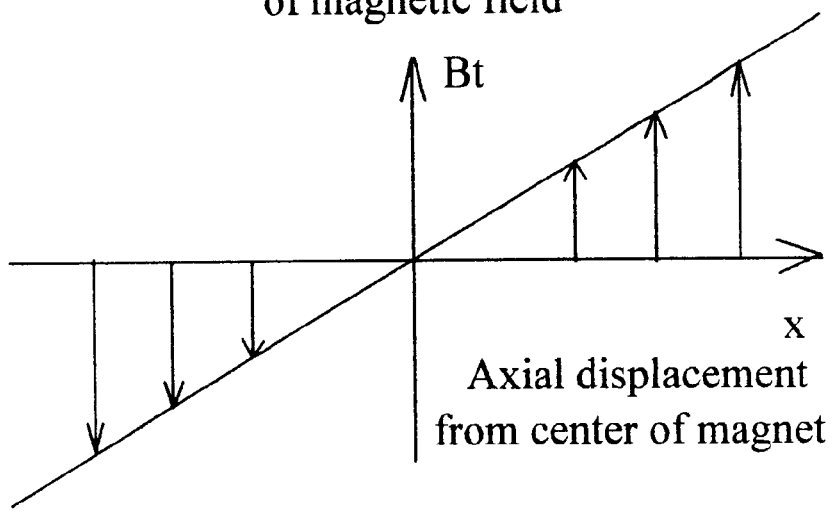
FIG. 4 is a diagram that shows the linearity of the radial (transverse) component of the magnetic field as a function of the longitudinal axial displacement as measured from the center of the magnet.
Figure 5:
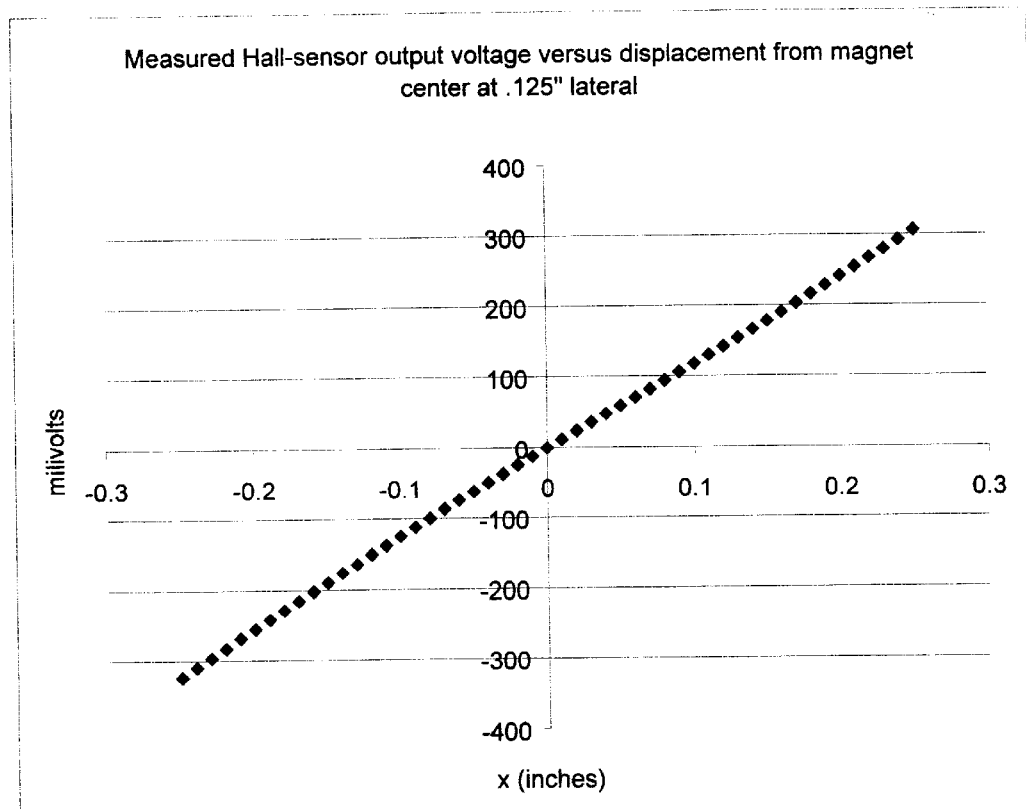
FIG. 5 is a diagram that shows an actual measured output voltage of a Hall sensor in a lateral slide-by approach as it slides-by a cylindrical bar magnet within the confine s of the poles of the magnet (within 80% of the length of the magnet), thus illustrating the axial linearity of the radial (transverse) component of the magnetic field as shown in FIG. 4.

In FIG. 3, two Hall-effect sensors 16 and 18 are shown on opposite lateral sides of a permanent bar magnet 24 whose north N and south S poles are shown; the preferred embodiment for the case of two sensors is that they be diametrically opposite each other. A cross section view of the magnetic field vector B 38 associated with this particular magnet is shown along with the resolution of this field vector B into its axial component Ba and its radial (transverse) component Bt 32. Using a preferred mathematical evaluation of the optimal length to diameter ratio of the bar magnet (generally about 4 to 1), the particular magnetization characteristics of this magnet is such that the magnitude of the transverse component Bt 32 can be configured to be linearly proportional to the longitudinal axial displacement x as measured from the center of the magnet 24—this to linear relation is illustrated in FIG. 4. Thus, as the magnet 24 moves axially in the longitudinal x-direction in a slide-by motion with respect to the two Hall sensors 16 and 18, which are fixed in the sensor fixture 10, the transverse magnetic field which intercepts the sensitive plane of the sensors is linear with respect to the axial displacement x of the magnet. Thus, the transverse field magnitude Bt equals the product of the two terms x and K (Bt=Kx), where x is the axial displacement measured from the center of the magnet, and K is a constant which depends upon the material make-up of the magnet, the sensitivity of the Hall-sensors, and the lateral displacements d1 and d2 of each sensor measured from the peripheral surface of the magnet. The net result is that the monitored output voltage, from each Hall sensor 16 and 18, is linearly proportional to the longitudinal axial displacement x of the magnet 24. Thus, with the two Hall sensors 16 and 18 positioned in the sensor wells on the stationary sensor fixture 10 in the preferred embodiment, any relative slide-by motion, within the borehole 19, of the actuator rod with the embedded magnet 24 provides a novel mechanism for obtaining a voltage whose magnitude is linear with respect to the longitudinal axial displacement x of the actuator rod. The quality of the linearity drops off significantly if the linear excursion between the center position of the Hall sensors and the center of the magnet goes beyond the limits of one-half of 80% of the length of the magnet. Thus, for reasonable displacements of the actuator rod (plus or minus 40% of the length of the magnet), the device proves to be an excellent linear displacement transducer. FIG. 5 shows the actual measured magnitude of the averaged output voltage of two Hall sensors positioned diametrically opposite each other on a sensor fixture as an actuator rod with an embedded bar magnet moves through the borehole in the longitudinal axial x-direction (x measured from the center of the Hall sensors) in a slide-by approach between two sensors. The graph shows measurements made at discrete (non-continuous) points and it illustrates a remarkable degree of linearity with respect to the axial displacement x.

In this invention, the preferred embodiment of two Hall sensors 16 and 18 diametrically situated on opposite sides of the cylindrical sensor fixture 10 along with the concentric slide-by movement of the magnet and the signal processing (averaging) of the output voltages constitute the slide-by push-pull operation of the linear displacement transducer system. The borehole 19, within the interior of the cylindrical sensor fixture 10, allows for passage of a moveable actuator rod 20 and the embedded permanent magnet 24 in the preferred lateral slide-by approach. FIG. 3 shows that as the magnet 24 moves axially through the cylinder, the transverse magnetic field Bt, which intercepts the sensitive plane of each Hall-sensor 16 and 18, varies with the axial displacement of the magnet, in addition to the lateral displacement d1 and d2 of each sensor, as measured from the sides of the magnet 24. Ideally, in a perfectly concentric and aligned system, the two lateral displacements d1 and d2 should remain constant and equal to each other. In reality, variances in the machining of the objects gives rise to misalignments and this is cause for the lateral displacements d1 and d2 to vary. To minimize this effect, this invention is structured such that the sum of the two lateral displacements (d1+d2) stays constant.

FIG. 3 shows that if the magnet 24 pushes away from one sensor 16 (d1 increases), it correspondingly pulls closer to the other sensor 18 (d2 decreases) such that the sum (d1+d2) stays a constant. Thus, by averaging the output voltages of the Hall sensors, the push-pull configuration provides a voltage that is only dependent upon the longitudinal axial displacement of the actuator; i.e. independent of the variations in the lateral displacements. Since it was shown earlier that the output voltage of each sensor is linear with respect to the axial displacement, then the average voltage is independent of the lateral displacements of each sensor and dependent only upon the axial displacement of the actuator rod. The incorporation of the slide-by-push-pull configuration along with the voltage averaging signal conditioner constitutes the preferred embodiment of the linear displacement transducer portion of this invention.

The above is a detailed description of the linear displacement transducer portion of this invention that plays an integral part in the operation of this liquid density/liquid level meter. The following is the description of the spring-float portion of this invention. There are two possible configurations of the spring-float portion of this invention. In the first configuration, which is the application-configuration for the liquid density meter shown in FIG. 6, two floats are used and these floats are coupled together with an actuator rod that is sandwiched between the two floats. In the second configuration, which is the application-configuration for the liquid level meter shown in FIG. 7, only a single float is used with the actuator rod attached at one end.

Figure 6:
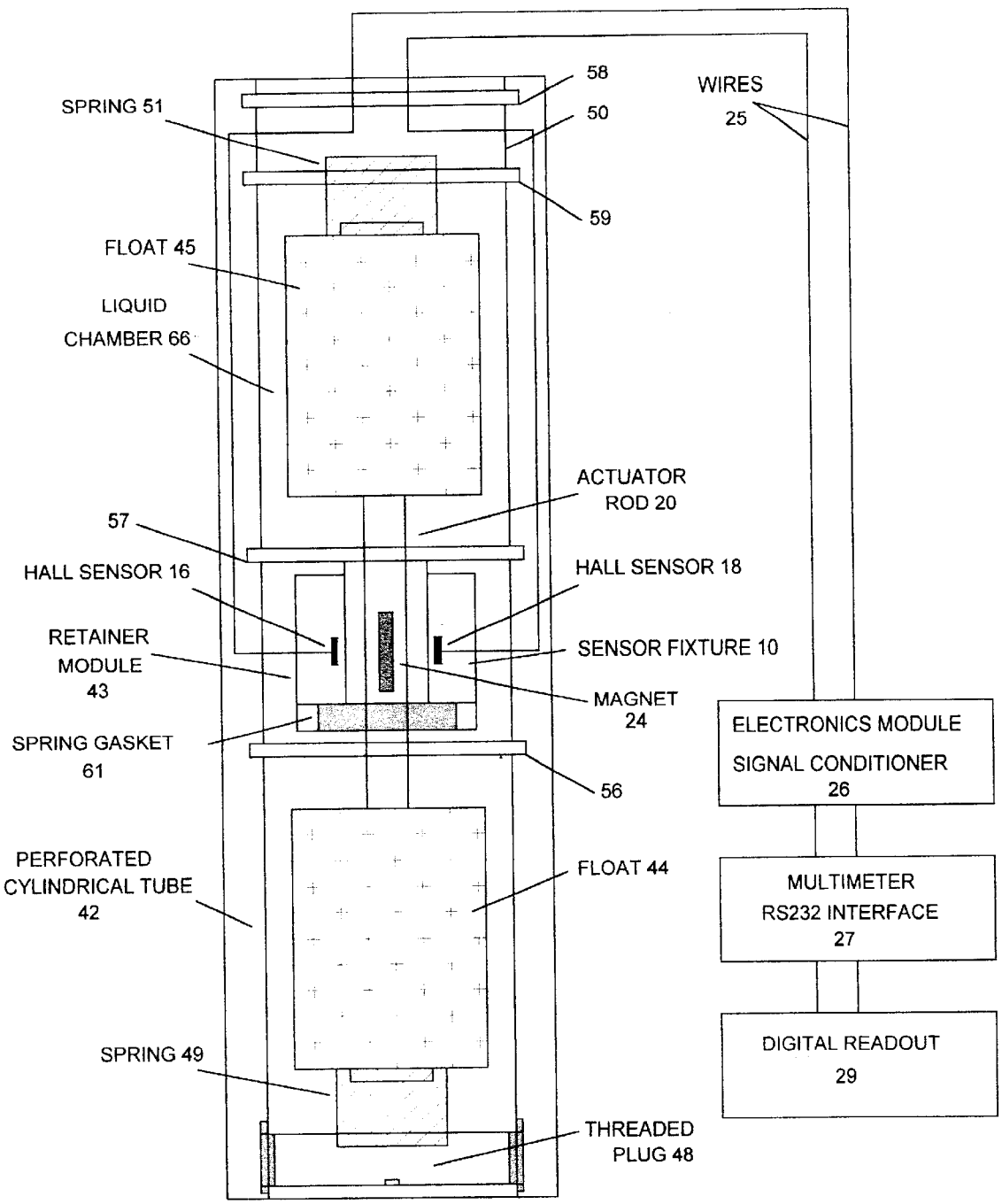
FIG. 6 is a diagram that shows the preferred embodiment of the submersible head unit in the liquid density meter configuration, which uses two cylindrical floats, constrained by two springs and a sandwiched actuator rod. The output of the head unit is communicatively connected to a remote electronics signal conditioner module.

The liquid density meter configuration shown in FIG. 6 has two cylindrical floats 44 and 45 that are connected by way of an actuator rod 20 that is sandwiched between the two floats. The actuator rod 20 contains an embedded magnet 24 that is aligned axially within the rod. The transducer sensor fixture 10, containing two (or more) Hall sensors 16 and 18, is situated within a fixture retainer module 43 that is positioned between the two floats. The retainer module 43 holds the sensor fixture 10 at the center and within the concentric confines of the perforated cylindrical tube 42. The retainer module 43 also contains a spring-gasket 61 that holds the sensor fixture firmly within the retainer. The spring-gasket 61 compresses the sensor fixture against the back wall of the retainer module and eliminates any random motion or chattering of the fixture within the module. The retainer module is held in place within the perforated cylindrical tube 42 by way of retainer clips 56 and 57. Within the perforated cylindrical tube 42 are two cylindrical floats 44 and 45 that are concentrically coupled to each other by way of the mutually attached actuator rod 20. Two springs 49 and 51 are on opposite sides of each float and these springs are held in place by the two end plugs 48 and 50. The two springs provide the necessary compression force along the axial direction of the perforated cylindrical tube needed to maintain the linearity of the longitudinal position of the float-actuator rod system when immersed in a liquid. These springs also help to provide the necessary lateral forces needed to maintain concentricity of the float-actuator rod system within both the borehole 19 and cylindrical tube 42. The two springs 49 and 51 have a very specific combined (summed) spring constant; this combined spring constant has a value such that the vertical gravitational drop of the suspended combined float and actuator rodmagnet system, when measured in air, is less than 40% of the length of the magnet 24. The end plug 50 and the threaded plug 48 have recessed seats to hold the springs 51 and 49, respectively, in place. The end plug 50 is held concentrically within the perforated cylindrical tube 42 with retainer clips 58 and 59. The threaded plug 48 is threaded into the end of the perforated cylindrical tube 42 and the purpose of this thread is to allow for the fine adjustment of the initial position of the center of the magnet with respect to the Hall sensors 16 and 18.

When the perforated cylindrical tube 42 is immersed in a liquid in a vertical fashion, the liquid is allowed to flow through the perforations into the liquid chamber 66. For operation of the liquid density meter, the perforated cylindrical tube 42 is deep enough into the liquid so that, at the least, the entire liquid chamber 66 is filled with the liquid. The liquid fills the liquid chamber 66 and produces a buoyancy force on the cylindrical floats 44 and 45 and the actuator rod 20 that causes the floats and the actuator rod 20 to rise. The liquid buoyancy force has a magnitude that is approximately equal to the weight of the liquid that is displaced by the floats and the actuator rod when all are completely immersed in the liquid (we assume the buoyancy of the springs to be negligible). Since the actuator rod 20 with the embedded magnet 24 is attached to the floats, then as the floats rise, the magnet is pushed higher into the proximity-sensing region of the linear displacement transducer. The larger the density of the liquid, the larger the buoyancy force, the higher the rise of the floats, and the higher the magnet moves into the proximity sensing region of the linear displacement sensor. This, in turn, produces a higher commensurate output voltage from each of the Hall sensors within the transducer. Since the buoyancy force is linear with respect to the density of the liquid, and the displacement of the spring supported floats is linear with respect to the buoyancy force, and the sensor output voltage is linear with respect to the displacement of the magnet within the proximity sensor, then the end result is that the output voltage is linear with respect to the density of the liquid—the preferred operational behavior of the liquid density meter. The Hall sensors are connected, by way of connector wires 25, into the electronics module 26 that contains the signal conditioner in addition to the power source for the sensors. With the proper initialization and preferred combinations of float density, liquid buoyancy, and spring constants for springs 49 and 51, the final output of the electronics module is made to give a direct measure of the density (specific gravity) of the liquid.

The preferred mathematical embodiment for the liquid density meter requires the combined buoyancy force of the cylindrical floats 44 and 45 and actuator rod 20, when totally immersed in pure water (specific gravity equal to 1), to be equal to the combined sum of the gravitational weights of the floats 44 and 45 and the actuator rod 20 and the magnet 24, when measured in air, plus the total spring force (the sum of the forces exerted by the two springs 49 and 51) exerted on the floats 44 and 45 when this combination hangs on the two springs 49 and 51 in air. We assume the buoyancy force due to the air to be negligible and we also assume the buoyancy force of the springs in the liquid and the weight of the springs to be negligible.

When the floats and all attachments are hung on the springs in air, the vertical gravitational drop displacement distance has a magnitude wherein the bar magnet, which is attached to the floats, displaces with respect to the Hall-sensors such that the Hall-sensors stay within the restrictive confines of the magnet; i.e. between the north and south poles and within 80% of the length of the magnet and at a lateral distance a fraction of the width or diameter of the magnet.

The initialization of this configuration for the liquid density meter entails two constraints: a) when the head unit sits vertically in air (no liquid), the output reads 0 and b) when the head unit sits vertically and totally immersed in pure water, the output reads 1 (the specific gravity of water). The judicious choice of system components, which is consistent with the preferred embodiment as explained in the above, will force the system to meet these constraints. The electronics module contains a signal conditioner that averages the Hall-sensor voltages and provides gain and initialization controls that contribute to compensating for any offset voltages of the Hall-sensors in meeting these two constraints.

Figure 7:
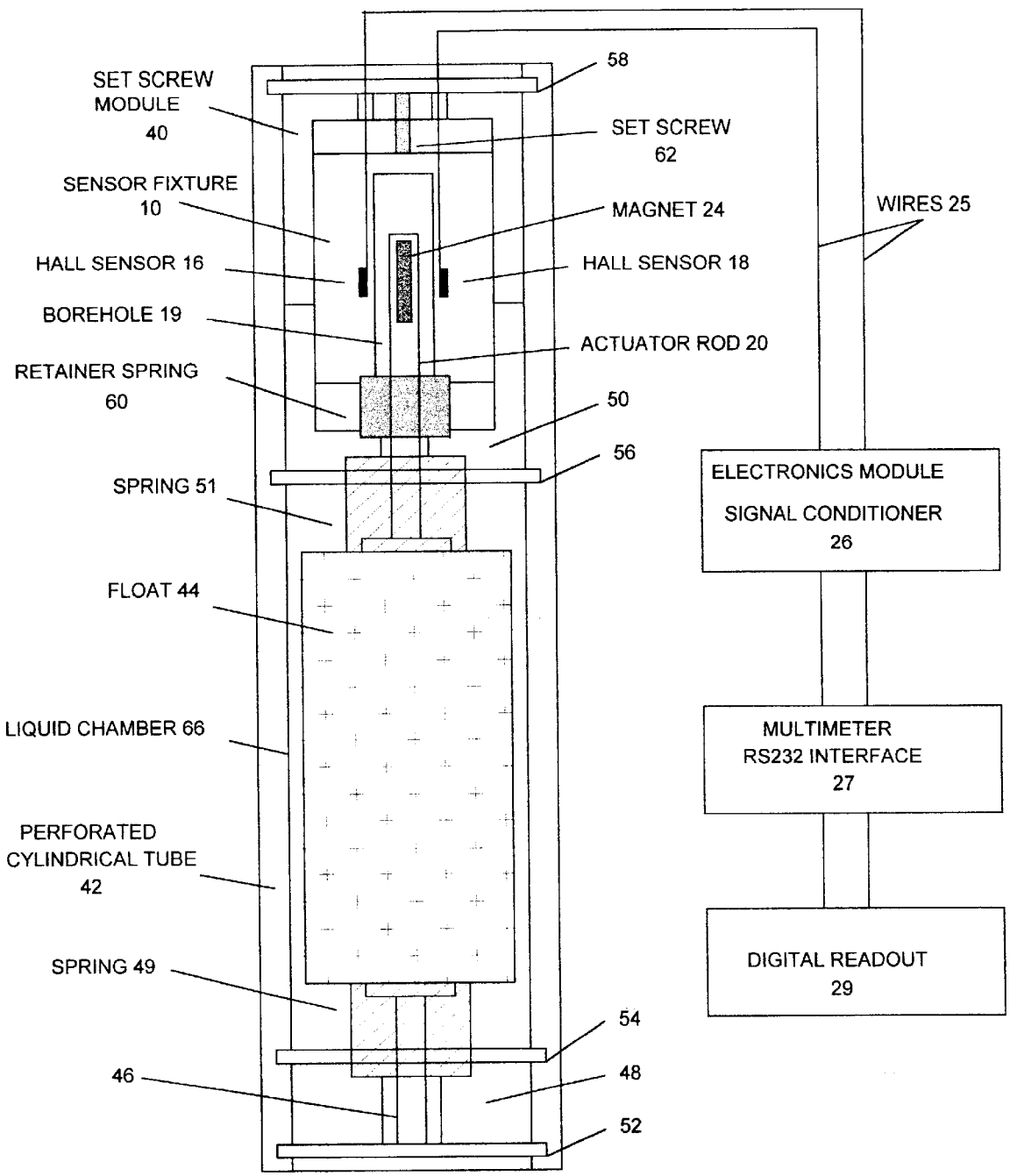
FIG. 7 is a diagram that shows the preferred embodiment of the submersible head unit in the liquid level meter configuration, which uses a single cylindrical float, constrained by two springs and an actuator rod. The output of the head unit is connected by wires to a remote electronics signal conditioner module.

The liquid level meter configuration shown in FIG. 7 shows a single cylindrical float that is constrained by two springs and to which is attached the actuator rod with an embedded magnet at one end. FIG. 7 shows the transducer sensor fixture 10 containing two (or more) Hall sensors 16 and 18 situated within a setscrew module 40. The setscrew module 40 is a mechanism for containing the sensor fixture 10 within the concentric confines of the perforated cylinder tube 42 and it contains a setscrew arrangement that allows for the fine-tuning of the position of the sensor fixture 10 relative to the magnet 24. Within the perforated cylindrical tube 42 is the linear displacement transducer along with the components that make up the float mechanism portion of this invention. Within the perforated cylinder tube 42 are the float 44 with its attached guide rod 46 and attached actuator rod 20, the plugs 48 and 50, and the two springs 49 and 51. The two springs provide the necessary compression force along the axial direction of the perforated cylindrical tube needed to maintain the linearity of the longitudinal positions of the float-actuator rod system when immersed in a liquid. The plugs 48 and 50 have concentric boreholes that force the guide rod 46 and the actuator rod 20 to remain concentric within both the perforated cylindrical tube 42 and the borehole 19 within the sensor fixture 10. In addition, these plugs have recessed seats to hold the springs in place.

The guide rod 46 and the actuator rod 20 are concentrically attached to the cylindrical float 44 in a manner such that when these rods move through the centers of the constraining plugs, the float stays at the center and remains concentric to the perforated cylinder tube. Two springs 49 and 51 cradle the guide rod 46 and the actuator rod 20, respectively, between the float and the constraining plugs 48 and 50. The plugs are held concentrically within the perforated cylindrical tube 42 with retainer clips 52, 54, and 56. The retainer clip 58 holds the setscrew module 40 in place. The Hall sensor fixture 10 is held longitudinally within the setscrew module 40 by way of a retaining spring 60 that backs up against the constraining plug 50 and which forces the sensor fixture 10 to hit up against the setscrew 62. As the setscrew 62 is adjusted, the sensor fixture 10 is allowed to slide concentrically within the setscrew module 40. This fine-tuning adjustment capability is the preferred embodiment used to initialize the position of the center of the permanent magnet 24 with respect to the geometric center of the Hall sensors 16 and 18.

When the perforated cylindrical tube 42 is immersed vertically in a liquid inside of a container, the liquid is allowed to flow through the perforations into the liquid chamber 66. The liquid enters the liquid chamber 66 to a level, which is equal to the level of penetration of the liquid chamber into the container. The liquid in the liquid chamber 66 produces a buoyancy force on the cylindrical float 44 and the actuator rod 20 and forces the float and all its attachments to rise. Since the actuator rod 20 is attached to the float on one end and the embedded bar magnet 24 on the other end, then as the float rises, the magnet is pushed higher into the proximity-sensing region of the linear displacement transducer. This, in turn, produces a rise in the output voltage from each of the Hall sensors within the transducer. Since the buoyancy force is linear with respect to the level of penetration of the cylindrical float in the liquid, and the displacement of the spring supported float is linear with respect to the buoyancy force, and the sensor output voltage is linear with respect to the displacement of the magnet within the proximity sensor, then the end result is that the output voltage is linear with respect to the level of penetration of the float within the liquid -the preferred operational behavior of the liquid level meter. The Hall sensors are connected, by way of connector wires 25, into the electronics module 26 that contains the signal conditioner circuit in addition to the power source for the sensors. With the proper initialization and preferred combinations of float density, liquid buoyancy, and spring constants for springs 49 and 51, the final output of the electronics module gives a direct measure of the level of the liquid in the container.

The preferred mathematical embodiment for the liquid level meter requires the combined buoyancy force of the cylindrical float 44 and the actuator rod 20 and the guide rod 46, when totally immersed in the liquid (the liquid is identified by its particular specific gravity), to be equal to the combined sum of the gravitational weights of the float 44 and the actuator rod 20 and the guide rod 46 and the magnet 24, when measured in air, plus the total spring force (the sum of the forces exerted by the two springs 49 and 51) exerted on the float 44 when this combination hangs on the two springs 49 and 51 in air. We assume the buoyancy force due to the air to be negligible and we also assume the buoyancy force of the springs in the liquid and the weight of the springs to be negligible.

When the float, and all its attachments, is hung on the springs in air, the vertical gravitational drop displacement distance is of a magnitude wherein the bar magnet, which is attached to the float, displaces with respect to the Hall-sensors such that the Hall-sensors stay within the restrictive confines of the magnet; i.e. between the north and south poles and within 80% of the length of the magnet and at a lateral distance a fraction of the width or diameter of the magnet.

The initialization of this configuration for the liquid level meter entails two constraints: a) when the head unit sits vertically in air (no liquid contact), the output reads 0 and b) when the unit sits vertically in the liquid in the container and the liquid chamber 66 penetrates the liquid in the container to the level where the chamber is just filled with the liquid, then the output reads the vertical level of penetration of the chamber 66 in the liquid. The judicious choice of system components, that is consistent with the preferred embodiment as explained in the above, will force the system to meet these constraints. The electronics module contains a signal conditioner that averages the Hall-sensor voltages and provides gain and initialization controls that contribute to compensating for any offset voltages of the Hall-sensors in meeting these two constraints.

FIGS. 6 and 7 show the two different possible configurations of the spring-float system of the submersible head unit when connected to the remote electronics module 26. The electronics module 26 contains the power source for operation of the Hall sensors in addition to the signal conditioner that averages the output voltages of all the Hall sensors. The signal conditioner allows for control of the initialization and gain of the averaged output voltage. The electronics module provides a digital readout of either 1) the density (specific gravity) of the liquid when the unit is configured as a liquid density meter, or 2) the level of the liquid in a container when the unit is configured as a liquid level meter. In addition to the digital readout, the electronics module also provides an analog output that can be configured with an RS232 interface 27 to provide a digital input signal to a computer 29. The computer generally contains software that allows for both the monitoring and the spreadsheet recording of the density or level of the liquid in addition to the temperature of the liquid by way of a connected thermocouple.

The preferred embodiments of the components in this invention are to be construed in the most general sense in that the springs referred to can be of the helical type or of the conical type or of the wafer type and that the bar magnet can be of the cylindrical type or the rectangular type. Furthermore, multiple units of Hall-sensors can be configured within the sensor fixture. In addition, all materials used within this invention are preferably variable such that they are compatible with the particular liquids within which they are immersed.

This invention has been described in a manner of detail that is presently considered to be the most practical and preferred embodiments and it is to be understood that the invention is not to be limited to the disclosed embodiments and that practitioners in the art will recognize that changes may be made in a form and detail without departing from the spirit and scope of the invention. For example, while the preferred embodiments were described as having two Hall sensors, any other number of Hall sensors may be utilized, such as three, four, etc., while remaining within the scope of the invention. These Hall sensors would preferably be evenly-spaced apart from each other on the sensor fixture. Also, the number of floats utilized may be different from the number described with respect to the preferred embodiments of the liquid level meter and the liquid density meter, while remaining within the scope of the invention.

What is claimed is:

1. A liquid density/liquid level meter, comprising:
    a spring-float portion that includes a plurality of springs and at least one float, the plurality of springs constraining movement of the at least one float;
    a linear displacement transducer portion that includes a magnet and a plurality of Hall sensors; and
    a submersible head unit that is adapted to couple the spring-float portion with the linear displacement transducer portion,
    wherein, when the submersible head unit is immersed in a liquid, the spring-float portion moves causing displacement of the magnet, thereby interacting with the plurality of Hall sensors in a lateral slide-by manner, so as to produce a voltage that is linear with respect to the displacement of the magnet,
    wherein the plurality of Hall sensors are disposed on the linear displacement transducer portion such that the plurality of Hall sensors are substantially equidistant with respect to the magnet.

2. A liquid density/liquid level meter according to claim 1, wherein the at least one float is disposed at one end of the spring-float portion.

3. A liquid density/liquid level meter according to claim 2, wherein the at least one float includes a first float positioned at a first end of the spring-float portion, and a second float positioned at a second end of the spring-float portion opposite the first end.

4. A liquid density/liquid level meter according to claim 1, further comprising:
    a remote electronic unit that receives the analog voltage and that provides a digital readout corresponding to either a density of the liquid or the level of a liquid in a container.

5. A liquid density/liquid level meter according to claim 4, wherein the remote electronic unit receives the analog voltage from the submersible head unit by one of a wired and a wireless connection.

6. A liquid density/liquid level meter according to claim 1, wherein the spring-float portion further comprises:
    a float-activated actuator rod,
    wherein the magnet is embedded in the float-activated rod,
    wherein the magnet moves in accordance with a combination of: a) a buoyancy force of the liquid, b) spring constants of the plurality of springs, and c) density of the at least one float, and
    wherein the magnet is a bar magnet.

7. A liquid density/liquid level meter according to claim 6, wherein the magnet has one of a rectangular and a cylindrical shape.

8. The liquid density/liquid level meter according to claim 6, wherein the float-activated actuator rod is only capable of movement along a longitudinal axis of the float-activated actuator rod, the movement being within the submersible head unit.

9. The liquid density/liquid level meter according to claim 1, wherein the voltage is linear with respect to an axial displacement center of the magnet as measured by the Hall sensors along a line that is lateral and parallel to a sensitive plane of the Hall sensors.

10. A liquid density/liquid level meter, comprising:
    a cylindrical unit that has a borehole therewithin, the cylindrical unit having a first recessed area and a second recessed area on an outer surface thereof;
    a first Hall sensor adapted to mount within the first recessed area;
    a second Hall sensor adapted to mount within the second recessed area;
    an actuator rod configured to move axially within the borehole of the cylindrical unit, wherein the actuator rod includes a non-magnetic region and a magnetic region,
    wherein, based on at least one of a density and a specific gravity of a liquid in which the liquid density meter is immersed, the actuator rod moves axially within the borehole to a particular position, thereby causing the first and second Hall sensors to respectively output first and second voltage signals based on proximity of the first and second Hall sensors to the magnetic region of the actuator rod,
    wherein the first and second voltage signals are utilized to determine the at least one of the density and the specific gravity of the liquid.

11. The liquid density/liquid level meter according to claim 10, further comprising:
    a housing that the cylindrical unit, the first and second Hall sensors, and the actuator rod are positioned therewithin;
    a plurality of springs that are respectively coupled to the actuator rod at opposite ends of the actuator rod,
    wherein the plurality of springs maintain the actuator rod at a precise central position within the borehole while allowing the actuator rod to move axially within the borehole.

12. The liquid density/liquid level meter according to claim 10, further comprising:
    a first float coupled to a first end of the actuator rod; and
    a second float coupled to a second end of the actuator rod,
    wherein the first and second floats cause the actuator rod to move upwards a particular amount based on the density and specific gravity of the liquid in which the floats are immersed.

13. The liquid density/liquid level meter according to claim 10, further comprising:
    a float coupled to one end of the actuator rod,
    wherein the float causes the actuator rod to move upwards a particular amount based on a level of the liquid in a container within which the liquid level meter is immersed.

14. A liquid density/liquid level meter, comprising:
    a cylindrical unit that has a borehole therewithin, the cylindrical unit having a first recessed area and a second recessed area on an outer surface thereof;
    a first Hall sensor adapted to mount within the first recessed area;

a second Hall sensor adapted to mount within the second recessed area;

an actuator rod configured to move axially within the borehole of the cylindrical unit, wherein the actuator rod comprises:
   a magnetic region; and
   a non-magnetic region that includes a float, wherein, based on a level of a liquid in a container within which the liquid level meter is immersed, the actuator rod moves axially within the borehole to a particular position due to the float floating within the liquid, thereby causing the first and second Hall sensors to respectively output first and second voltage signals based on proximity of the first and second Hall sensors to the magnetic region of the actuator rod, and wherein the first and second voltage signals are utilized to determine the level of the liquid.

15. The liquid density/liquid level meter according to claim 1, wherein the liquid density or the liquid level of the liquid is determined by summing an output from each of the plurality of Hall sensors, and wherein an average of the summed outputs corresponds to the liquid density or the liquid level of the liquid.

16. The liquid density/liquid level meter according to claim 1, wherein the plurality of Hall sensors include at least one pair of Hall sensors that are disposed on the submersible head unit in a manner such that when the submersible head unit is not immersed in the liquid, the magnet is disposed directly between the at least one pair of Hall sensors.

17. The liquid density/liquid level meter according to claim 1, wherein the plurality of Hall sensors are disposed on the submersible head unit such that the magnet is capable of sliding movement in a space between the at least one pair of Hall sensors.

18. The liquid density/liquid level meter according to claim 1, wherein the plurality of springs have a spring force so as to maintain a maximum vertical excursion of the spring-float portion to be within 80% of a total length of the magnet.

* * * * *